US010653818B2

(12) United States Patent
Yoon et al.

(10) Patent No.: US 10,653,818 B2
(45) Date of Patent: May 19, 2020

(54) MAGNETIC NANOPARTICLE EMBEDDED NANOFIBROUS MEMBRANE

(71) Applicant: University of Florida Research Foundation, Inc., Gainesville, FL (US)

(72) Inventors: Yong-Kyu Yoon, Gainesville, FL (US); Sheng-Po Fang, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 594 days.

(21) Appl. No.: 15/113,633

(22) PCT Filed: Jan. 23, 2015

(86) PCT No.: PCT/US2015/012605
§ 371 (c)(1),
(2) Date: Jul. 22, 2016

(87) PCT Pub. No.: WO2015/112812
PCT Pub. Date: Jul. 30, 2015

(65) Prior Publication Data
US 2017/0239393 A1    Aug. 24, 2017

Related U.S. Application Data

(60) Provisional application No. 61/930,774, filed on Jan. 23, 2014.

(51) Int. Cl.
*A61L 27/44* (2006.01)
*A61L 27/50* (2006.01)
(Continued)

(52) U.S. Cl.
CPC .......... *A61L 27/446* (2013.01); *A61L 27/042* (2013.01); *A61L 27/18* (2013.01); *A61L 27/50* (2013.01);
(Continued)

(58) Field of Classification Search
CPC ..................... A61L 27/446; H05K 2201/05
(Continued)

(56) References Cited

U.S. PATENT DOCUMENTS 6,083,264 A    7/2000   Wood et al.
6,180,950 B1   1/2001   Olsen
(Continued)

FOREIGN PATENT DOCUMENTS

WO    2012140519 A2    10/2012
WO    2013181559 A1    12/2013

OTHER PUBLICATIONS

N. Bhattarai, D. Edmondson, O. Veiseh, F. A. Matsen, and M. Zhang, Biomaterials, vol. 26, No. 31, pp. 6176-6184, 2005.
(Continued)

*Primary Examiner* — Peter Y Choi
(74) *Attorney, Agent, or Firm* — Thomas | Horstemeyer, LLP (57) ABSTRACT

Various examples are provided for magnetic particle imbedded nanofibrous membranes. In one example, among others, a nanofibrous membrane includes one or more electrospun nanofibers forming form a layer of nanofibers, and a plurality of magnetic nanoparticles embedded in the one or more electrospun nanofibers. In another example, a method includes generating one or more electrospun nanofibers including magnetic nanoparticles from one or more nozzles positioned over a substrate to form a magnetic nanofibrous layer, and affixing the magnetic nanofibrous layer to a support structure. In another example, a system includes a magnetic nanofibrous membrane affixed to a support structure, and a magnetic field generator configured to generate a magnetic field that passes through the magnetic nanofibrous membrane.

16 Claims, 5 Drawing Sheets

(51) Int. Cl.

| | |
|---|---|
| *B82Y 30/00* | (2011.01) |
| *A61L 27/56* | (2006.01) |
| *D01D 5/00* | (2006.01) |
| *A61L 27/04* | (2006.01) |
| *A61L 27/18* | (2006.01) |
| *A61L 27/58* | (2006.01) |
| *D04H 1/728* | (2012.01) |

(52) U.S. Cl.
CPC .............. *A61L 27/56* (2013.01); *A61L 27/58* (2013.01); *B82Y 30/00* (2013.01); *D01D 5/0007* (2013.01); *D01D 5/0061* (2013.01); *D04H 1/728* (2013.01); *A61L 2300/102* (2013.01); *A61L 2400/12* (2013.01)

(58) Field of Classification Search
USPC .......................................................... 442/376
See application file for complete search history.

(56) References Cited

U.S. PATENT DOCUMENTS

| | | |
|---|---|---|
| 8,282,873 B2 | 10/2012 | Barinov et al. |
| 2006/0013869 A1 | 1/2006 | Ignatious et al. |
| 2006/0057377 A1 | 3/2006 | Harrison et al. |
| 2009/0143227 A1 | 6/2009 | Dubrow et al. |
| 2009/0239338 A1 | 9/2009 | Zhou et al. |
| 2011/0111201 A1 | 5/2011 | Reneker et al. |
| 2012/0040581 A1 | 2/2012 | Kim |
| 2012/0329947 A1 | 12/2012 | Ziegler |

OTHER PUBLICATIONS

C. P. Barnes, S. A. Sell, E. D. Boland, D. G. Simpson, and G. L. Bowlin, Advanced Drug Delivery Reviews, vol. 59, No. 14, pp. 1413-1433, 2007.

O. Castaño, M. Eltohamy, and H.-W. Kim, Methods in Molecular Biology Nanotechnology in Regenerative Medicine Methods and Protocols, vol. 811, pp. 127-140, 2011.

S. Kim and C. B. Park, Advanced Functional Materials, vol. 23, No. 1, pp. 10-25, Jan. 2013.

V. I. Sikavitsas, G. N. Bancroft, and A. G. Mikos, Journal of Biomedical Materials Research, vol. 62, No. 1, pp. 136-148, 2002.

Y. Hu, D. W. Grainger, S. R. Winn, and J. O. Hollinger, Journal of Biomedical Materials Research, vol. 59, No. 3, pp. 563-572, 2002.

J. M. Razal, M. Kita, A. F. Quigley, E. Kennedy, S. E. Moulton, R. M. I. Kapsa, G. M. Clark, and G. G. Wallace, Advanced Functional Materials, vol. 19, No. 21, pp. 3381-3388, Nov. 2009.

J. T. Kannarkat, J. Battogtokh, J. Philip, O. C. Wilson, and P. M. Mehl, Journal of Applied Physics, vol. 107, No. 9, pp. 09B307-3, May 2010.

Y.-S. Lee and T. Livingston Arinzeh, "Electrospun Nanofibrous Materials for Neural Tissue Engineering," Polymers, vol. 3, No. 4, pp. 413-426, Feb. 2011.

C. Dang, N. Bhattarai, D. Edmondson, A. Cooper, and M. Zhang, Journal of Undergraduate Research in Bioengineenng, pp. 29-32, 2007.

M. A. Matos and M. T. Cicerone, Biotechnol Prog 2010; 26 (3): 664-670.

J.L. Pipkin, W. G. Hinson, J. F. Young, K. L. Rowland, J. G. Shaddock, W. H. Tolleson, P. H. Duffy, and D. A. Casciano, Bioelectromagnetics, pp. 347-357, Sep. 1999.

P. Clark, P. Connolly, A. S. G. Curtis, J. A. T. Dow, and C. D. W. Wilkinson, Journal of Cell Science 99, pp. 73-77, 1991.

Y. Yamada, G. Umegaki, T. Kawashima, M. Nagai, T. Shibata, T. Masuzawa, T. Kimura, and A. Kishida, J. Phys.: Conf. Ser., vol. 352, Conf. 1, 2012.

International Search Report for PCT/US2015/012605 dated Apr. 21, 2015.

|  | Nanofiber membrane | Solid PCL membrane |
|---|---|---|
| Density | 572.85 kg/m$^3$ | 1145 kg/m$^3$ |
| Porosity | 72% | 0% |
| Relative Permeability | 1.05-1.07 | 1 |
| Self-Resonant Frequency | 4.5 Hz | 80.5 Hz |
| Effective Young's Modulus | 0.127 MPa | 90 MPa |

FIG. 9

MAGNETIC NANOPARTICLE EMBEDDED NANOFIBROUS MEMBRANE

CROSS REFERENCE TO RELATED APPLICATIONS

This application claims priority to, and the benefit of, U.S. provisional application entitled "MAGNETIC NANOPARTICLE EMBEDDED NANOFIBROUS MEMBRANE" having Ser. No. 61/930,774, filed Jan. 23, 2014, which is hereby incorporated by reference in its entirety.

STATEMENT REGARDING FEDERALLY SPONSORED RESEARCH OR DEVELOPMENT

This invention was made with government support under agreement ECCS 1132413 awarded by the National Science Foundation. The Government has certain rights in the invention.

BACKGROUND

Technological innovations in various fields of electronics, optics, energy, medicine, and biology have inspired and pressed for the development of nanoscale functional materials in the various morphologies ranging from films and fibers to cones and coaxial spheres. Membranes can be generated with nanoscale fibers from electrospunnable polymer melts or solutions.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Disclosed herein are various examples related to magnetic particle imbedded nanofibrous membranes. Magnetic nanofibrous membranes can be generated using electrospinning of nanofibers. When embedded with magnetic particles, magnetically driven active nanofibers and nanofibrous membranes can be produced. For example, magnetic nanofibrous membranes can be used as active tissue scaffolds. A wirelessly driven active cell culture system can be advantageous since it can stimulate cells remotely. Magnetic nanofibrous membranes can also be used as, e.g., a speaker membrane or in other applications that can use a vibrating platform or screen. Porosity of the membrane can also be adjusted for the application.

Electrospun nanofiber can be utilized in many scientific disciplines and engineering applications primarily due to its nanoporous morphology, which includes unique physical and chemical properties that differentiate it from bulk materials. Nanofiber provides a large surface area which allows nanoparticles to transfer through. For tissue engineers, nanofiber offers great cell viability and density enhancement due to its nanoporous architecture. Nanofiber can serve as a mechanical support for the tissue, which enables cells to be attached and communicate each other. It has the potential to regulate the division, migration, and shape of the cell. Significant improvement of cell culturing on nanofibrous scaffolds is possible. A nanofiber scaffold is suitable for in vivo cell culture, especially for cells that require a highly porous and large surface area scaffold such as, e.g., bone cells. Biomaterial and tissue engineering fields can have a high demand for a fabricated biocompatible nanofiber scaffold that has the nanoporous morphology.

One application for a nanofiber scaffold is an in vitro tissue that can be implanted in vivo. Unlike a conventional passive scaffold, which only provides mechanical support of the cells, an active tissue scaffold with various external stimulation modalities (e.g., stress, strain, electrical, acid/base and optical field) can become increasingly important for advanced tissue engineering research. Such an active tissue scaffold can be especially useful for studying differentiation conditions of stem cells. Understanding the influence of different active stimulations on cell viability and differentiation is an important aspect of stem cell research.

Alignment of nanofibers in electrospinning can be accomplished using directional guided electrical fields. Cultured cells show directional growth, along the aligned nanofibers. Alternating external electric fields at low frequency can also enhance neural cell viability in the electrokinetically driven flow. The electrokinetical driven flow frequency can either enhance or suppress neural cell differentiation. The efficiency of stem cell harvesting may be maximized with 91.6-95% cell viability when cultured in a condition with a vibrating frequency of approximately 5 Hz.

The magnetic nanofibrous membranes can include electrospun nanofibers embedded with magnetic nanoparticles. In this disclosure, a mechano-active nanofibrous scaffold system, which can provide mechanical stress and strain on culturing cells by external AC magnetic fields, is discussed. The system can include an iron oxide nanoparticle embedded electrospun polycaprolactone nanofiber membrane, a membrane holder, and an external electromagnet producing AC magnetic fields. The system can be designed to operate at about 4.5 Hz and with a nominal displacement in the order of 100 nm.

The nanofibers can be generated from a polymer such as, e.g., polycaprolactone (PCL) or poly lactic-glycolic acid (PLGA). The magnetic nanoparticles can include magnetic elements such as, e.g., iron, nickel, cobalt, neodymium and/or their chemical compounds (e.g., cobalt iron oxide, nickel iron cobalt, cobalt iron boron and/or $FeO_3$). In some implementations, the electrospun nanofibers can have a diameter in a range of about 100 nm to about 1000 nm with magnetic particles with a diameter of less 100 nm or in a range of, e.g., about 1 nm to about 10 nm, about 1 nm to about 50 nm or about 1 nm to about 90 nm. One embodiment, among others, includes electrospun nanofibers comprising polycaprolactone and iron oxide nanoparticles. Other types of magnetic nanoparticles or combinations of magnetic nanoparticles may also be embedded in the electrospun nanofibers (e.g., NiFe nanoparticles). The magnetic nanofibrous membrane can be affixed to a support structure such as, e.g., a printed circuit board or a petri dish for support. The support structure may be configured to monitor the magnetic nanofibrous membrane. For instance, the support structure may include electrical traces to deliver or detect electrical signals to or from cells of the tissue on the magnetic nanofibrous membrane. The support structure may also include sensors for monitoring the magnetic nanofibrous membrane and/or the tissue.

The magnetic nanofibrous membrane can be utilized for, e.g., in vitro or in vivo active cell culture and stem cell differentiation. The magnetic nanofibrous membrane can be designed to have a specific resonant frequency (or range of frequencies), which may enhance or suppress cell culture and/or cell differentiation. For instance, operation in a range of about 4 Hz to about 5 Hz can be conducive to cell culture and/or differentiation. The magnetic nanofibrous membrane can also be designed for operation at other frequencies or over other frequency ranges, which are appropriate for the application. Magnetic nanoparticles can be heated using the core loss of the magnetic materials at high frequencies (e.g., at MHz and/or GHz frequencies). For example, the embedded nanoparticles can be energized in a GHz range to produce heat resulting from magnetic core loss, which will be used for hyperthermia treatment, drug releasing or a localized incubator. The magnetic nanoparticles may also be bonded to drugs or catalysts to give additional functions such as drug delivery, sensing, etc.

In one implementation, among others, a mechano-active nanofibrous scaffold system for in vitro active cell culture was fabricated using electrospun nanofibers with magnetic nanoparticles embedded, and an electromagnet. The electrospun nanofibers included polycaprolactone and iron oxide nanoparticles. The magnetic nanofibrous membrane was held by a micro-machined printing circuit board (PCB) O-ring and remotely actuated by an electromagnet, which generated alternating current (AC) magnetic fields. The scaffold provided mechanical stress and strain on culturing cells in response to the external AC magnetic fields. Mechanical properties of the magnetic nanoporous membrane (e.g., density, porosity, and effective Young's modulus) were characterized. Cell viabilities on the nanofibrous membrane with and without embedded magnetic nanoparticles were tested.

Figure 1:
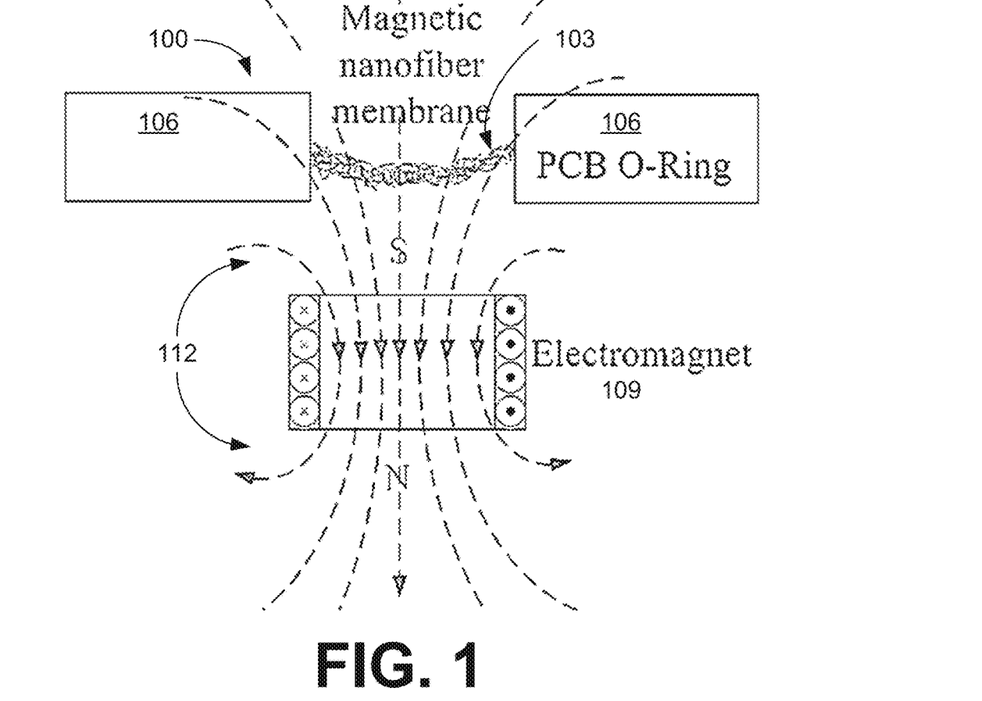
FIG. 1 is a graphical representation illustrating a magnetic nanofibrous membrane in a magnetic field in accordance with various embodiments of the present disclosure.
Figure 2:
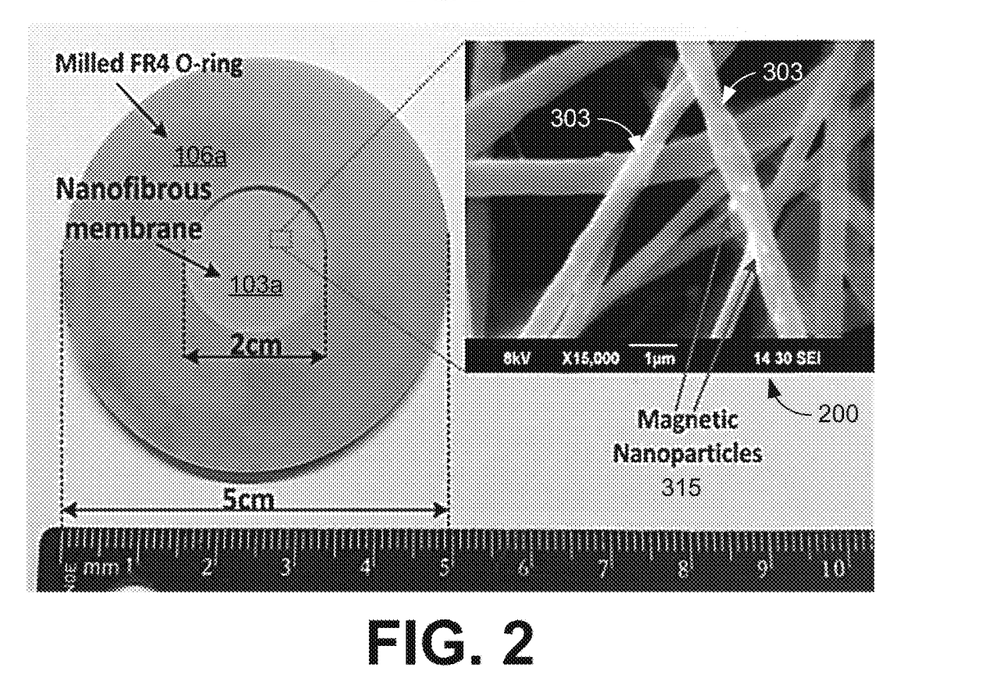
FIG. 2 is an image of an example of a magnetic nanofibrous membrane of FIG. 1 in accordance with various embodiments of the present disclosure.

Referring to FIG. 1, shown is a schematic diagram illustrating an example of an active magnetic nanofibrous scaffold system 100 including a magnetic nanofibrous membrane 103 supported by a structure 106 such as, e.g., a PCB O-ring. The magnetic nanofibrous membrane 103 can be placed above an electromagnet 109, which generates a magnetic field 112 for membrane actuation. For example, the nanofibrous membrane 103 can be placed about 2 cm above the electromagnet 109. The movement of the magnetic nanofibrous membrane 103 can be controlled by an AC magnetic field 112 of the electromagnet 109. FIG. 2 includes an image of a fabricated magnetic nanofibrous membrane 103a secured to a PCB O-ring 106a.

To study the effect of pure mechanical stimulation on cells, the external magnetic field 112 should be small. For example, the magnetic flux can be set to be less than 10 Gauss which is a typical electromagnetic (EM) value that human body may encounter in daily life. Cell viability and density can be improved with a mechanical oscillation in the range of about 50 nm to about 240 nm during culturing. Therefore, the targeted displacement can be 100 nm, with a designed frequency in the range of about 4 Hz to about 5 Hz. Typical human cells are in the range of about 10 µm in diameter, which can be 100 times larger than the designed displacement. Oscillating the cells within 1% of their volume size can prevent damaging cells during culturing. With the described design parameters, the dimension of the magnetic nanofibrous membrane 103 can be calculated to have a diameter of about 2 cm and a thickness of about 50 µm. The fine tuning of the displacement and resonant frequency can be obtained via numerical analysis using a physical modeling/simulation program such as, e.g., COMSOL Multiphysics®.

Referring now to FIGS. 3A through 3F, shown is an example of a process for fabrication of active magnetic nanofibrous membrane 103 on a support structure 106. Initially, a magnetic nanoparticle embedded polymer solution can be prepared by dissolving a biodegradable polymer in a solution, which is then mixed with magnetic particles. For example, polycaprolactone (PCL) (e.g., Sigma Aldrich Inc.), a biodegradable polymer, can be dissolved in dimethylformamide (e.g., Sigma Aldrich Inc.) and dichloromethane (e.g., Sigma Aldrich Inc.) for 24 hours to give a PCL solution concentration of about 16 wt/vol %. Then, 5 wt % of iron oxide nanoparticles (e.g., Sigma Aldrich Inc.) can be mixed with the PCL solution. The iron oxide nanoparticles can have an average diameter of less than 50 nm, which is also favorable to cell adhesion. The magnetic nanoparticle embedded polymer solution can be prepared by mechanically stirring the contents using a DC motor at 500 rpm in an air tight bottle.

Figure 3A:
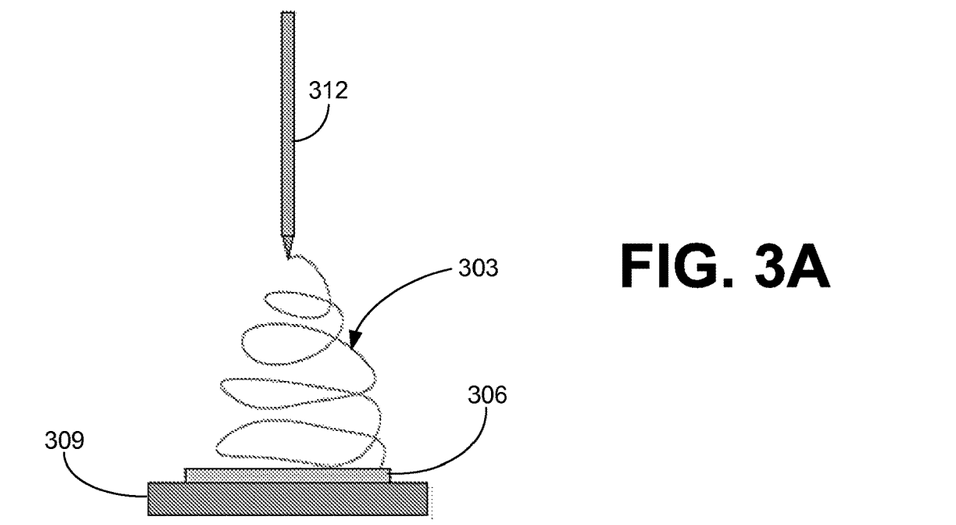
FIG. 3 illustrates an example of a fabrication process of the magnetic nanofibrous membrane of FIGS. 1 and 2 in accordance with various embodiments of the present disclosure.
Figure 3B:
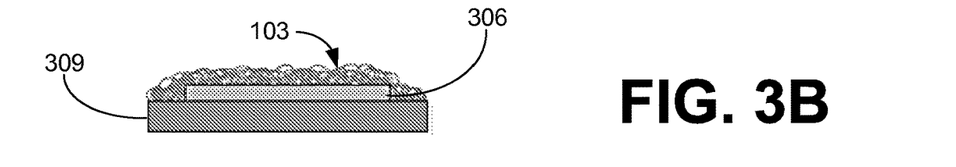

Beginning with FIG. 3A, magnetic nanofibers 303 are electrospun on a substrate 306 positioned on a ground collector 309. The magnetic nanoparticle embedded polymer solution can be ejected from a charged needle 312 towards the substrate 306 to form the nanofibrous membrane 103. Electric and/or magnetic fields can be used to control the orientation of the magnetic electrospun nanofibers 303. For example, the substrate 306 can be a silicon (Si) substrate. In one implementation, the magnetic nanoparticle embedded polymer solution can be dispensed for about 240 seconds to collect a 50 µm thick nanofibrous membrane 103 on a 2-inch Si substrate 306 as shown in FIG. 3B, using an electric field of 1.16 kV/cm and with the solution dispensed at a flow rate of 1 ml/min. The substrate 306 can then be separated from the ground collector 309.

Figure 3C:
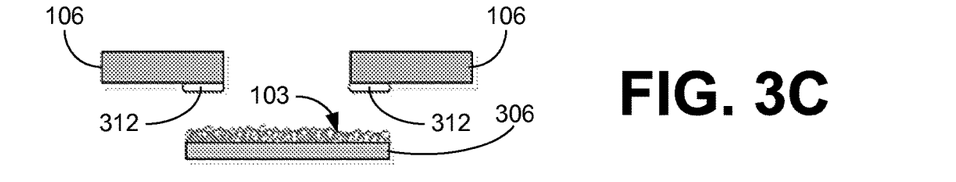
Figure 3D:
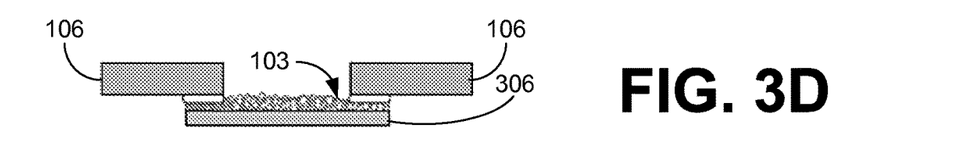

Next, a support structure 106 can be formed to hold the magnetic nanofibrous membrane 103. For example, an O-ring shape membrane holder can be machined out of printing circuit board (PCB). In the example of FIG. 2, the PCB O-ring 106a has an inner diameter of about 2 cm and an outer diameter of about 5 cm. Other shapes and dimensions can also be implemented for the support structure 106. Glue 312 such as, e.g., a non-toxic water soluble glue can be applied around at least a portion of the opening of the support structure 106 to secure the magnetic nanofibrous membrane 103 in place as shown in FIG. 3C. The support structure 106 (e.g., the O-ring holder) can be attached to the magnetic nanofibrous membrane 103 as shown in FIG. 3D. For instance, the support structure 106 can remain in position on the magnetic nanofibrous membrane 103 for about 2 hours to allow the glue 312 to dry.

Figure 3E:
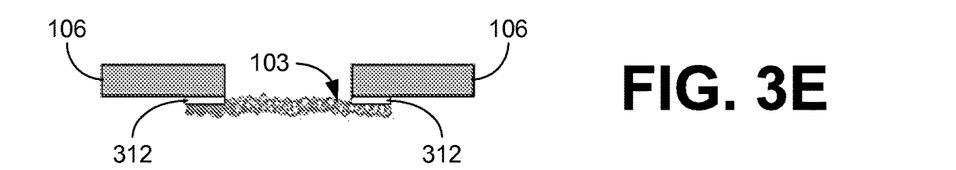
Figure 3F:
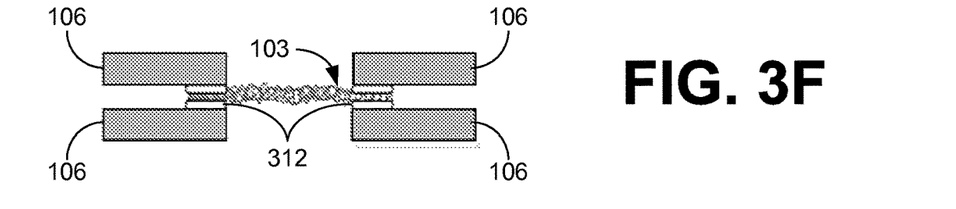

After the glue 312 has dried, the magnetic nanofibrous membrane 103 attached to the support structure 106 can be separated from the substrate 306 in FIG. 3E. In some embodiments, the magnetic nanofibrous membrane 103 can be sandwiched between two portions of the support structure 106 to increase stability. The two portions would be glued on opposite sides of the magnetic nanofibrous membrane 103 as illustrated in FIG. 3F. The fabrication process is scalable, manufacturable, and cost effective. The magnetic nanofibrous scaffold can be placed in vacuum for 24 hours to remove any solvents that remain in the nanofiber membrane 103.

Figure 4:
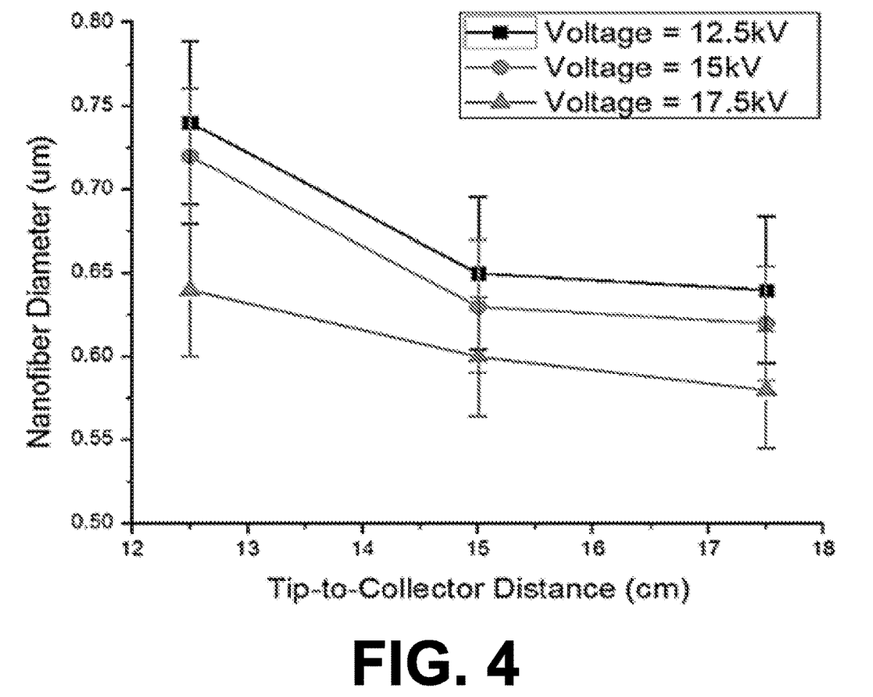
FIGS. 4-7 are plots of characteristics of various magnetic nanofibrous membranes in accordance with various embodiments of the present disclosure.

An image of a fabricated magnetic nanofibrous scaffold is shown in FIG. 2. The insert image 200 of FIG. 2 is a scanning electron microscope (SEM) (e.g., JEOL 5700) image of the magnified electrospun nanofibers 303 with magnetic particles 315 embedded therein. The SEM image 200 shows iron oxide nanoparticles embedded in polycaprolatone (PCL) nanofibers. Electrospinning was been performed under different electric field conditions, leading to various nanofiber diameters from 550±36 nm to 750±42 nm with the electric field varying from 0.7 kV/cm to 1.0 kV/cm, respectively. FIG. 4 is a plot illustrating the nanofiber diameter variation at different electric field strengths and different tip-to-collector distances.

Figure 5:
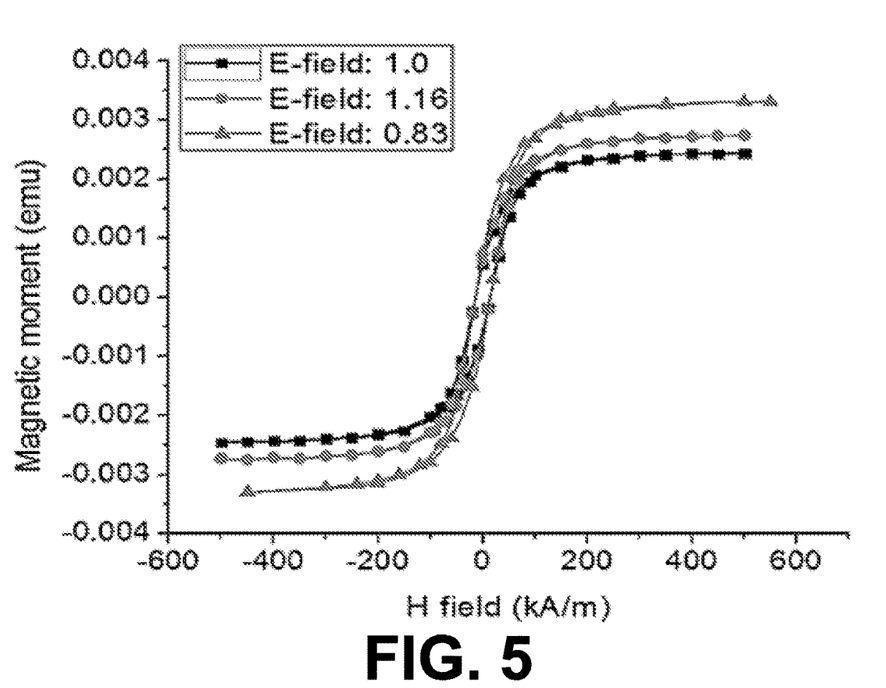

The hysteresis loops of the magnetic nanofibrous membranes produced with different electrical fields in electrospinning were measured using a Vibrating Sample Magnetometer (e.g., ADE technologies) with the magnetic field feeding perpendicular to the membrane (or out of plane feeding). Referring to FIG. 5, shown are the hysteresis loops plotted for three different magnetic nanofibrous membranes 103 with nanofibers collected by electrospinning with different electric field strengths: 1.16 kV/cm, 1 kV/cm, and 0.83 kV/cm. The magnetic moment and magnetic field relationship curve is shown in FIG. 5.

The effective relative permeability of a magnetic nanofibrous membrane 103 can be calculated with the hysteresis loop. The magnetization is defined by the magnetic moment divided by the sample volume as:

$$B = \mu_0(H+M) = \mu_0(H+XH) = \mu_0(1+X)H, \quad (1)$$

where the relative permeability is defined by:

$$\mu_r = 1 + X = 1 + \frac{M}{H}. \quad (2)$$

The calculated effective relative permeability varies from 1.05 to 1.07 for the electrospun fibers collected in an electric field of 1.16 kV/cm to 0.83 kV/cm, respectively. As increasing the electric field strength of electrospinning, the resultant nanofiber diameter decreases and the porosity of the membrane increases. Therefore, smaller amount of iron oxide nanoparticles are embedded in the membrane 103.

Figure 6:
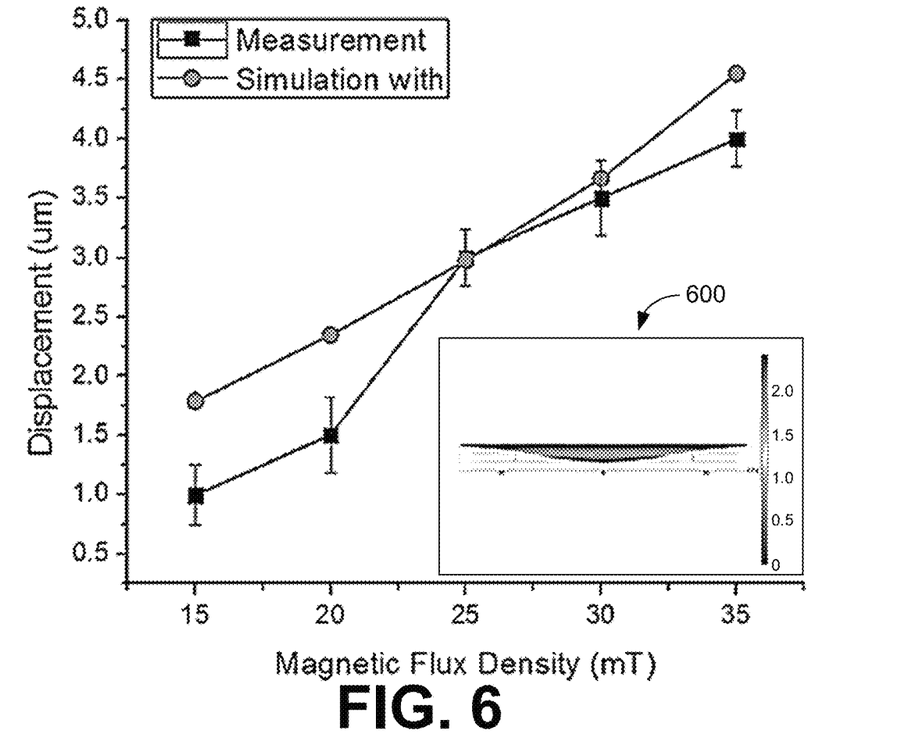

Referring to FIG. 6, shown are plots of simulated and measured maximum deflection of the magnetic nanofibrous membrane 103 responding to the DC magnetic field. The maximum displacement of the membrane 103 at the center responding to the DC magnetic field was simulated and measured, as shown in FIG. 6. The inset image 600 of FIG. 6 shows a simulation plot of a simulated and measured maximum deflection of the magnetic membrane 103. The maximum center deflection of the membrane 103 shows an almost linear relationship in the small deflection case. For example, the deflection changes from 1 μm to 4 μm as the magnetic flux density varies from 15 mT to 35 mT. The measurement result shows a similar trend and reasonably well matches with that of simulation.

Figure 7:
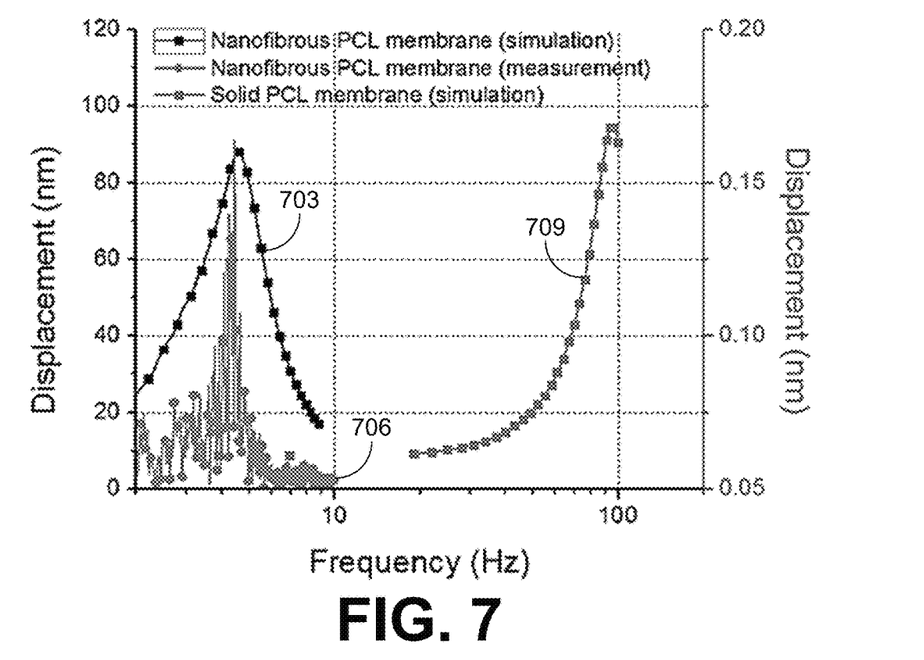

Referring now to FIG. 7, shown are the simulated and measured resonant frequencies of the nanofibrous membranes (703 and 706, respectively) compared to the simulated resonant frequency of a solid PCL membrane (709). FIG. 7 shows the AC response of the fabricated magnetic nanofibrous membrane 103 with a self-resonant frequency of 4.43 Hz, a maximum deflection of 91 nm, and a Q-factor of 14. A laser vibrometer (e.g., Polytec Inc.) was used for the displacement measurement. By fitting the simulated first self-resonant frequency to the measured self-resonant frequency, the effective Young's modulus of the nanofibrous magnetic membrane 103 was determined as 0.127 MPa.

A 5 day in vitro cell culture analysis was performed on the magnetic nanofibrous scaffold using mouse cells and cultured with Dulbecco's Modified Eagle Medium with Nutrient Mixture F-12 (DMEM/F12) and 10% phosphate buffered saline (PBS) solution. A cell viability test was performed with the mouse cells cultured for 5 days using the polycaprolatone nanofibrous membranes 103 with and without magnetic nanoparticles embedded. The external magnetic field was not applied in either case. The mouse cells were pre-cultured in Dulbecco's Modified Eagle Medium with Nutrient Mixture F-12 (DMEM/F12) and 10% PBS solution for 3 days to stabilize the condition and be ready to be seeded. Then, the cells were labeled with Dil and seeded on both the magnetic and non-magnetic nanofibrous membranes 103.

Figure 8:
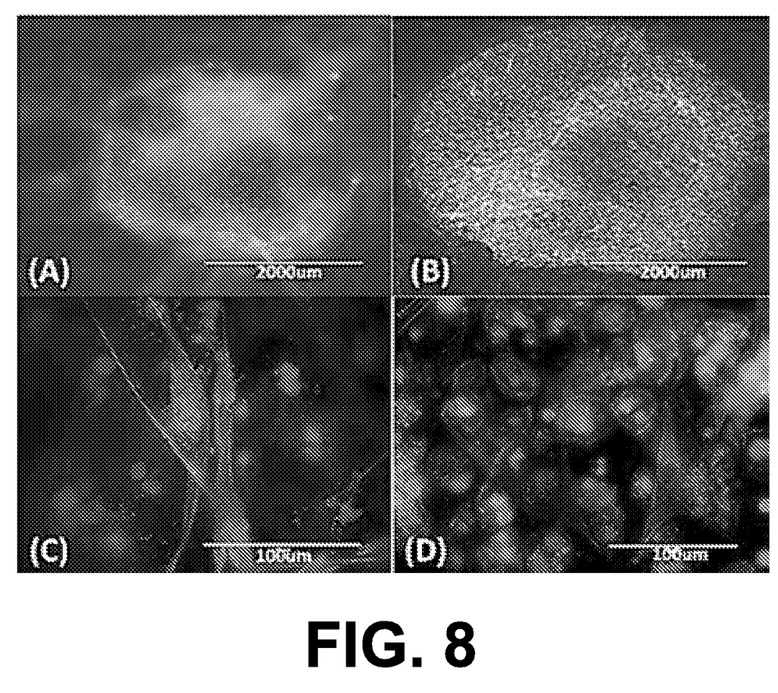
FIG. 8 includes images of examples of mouse cell viability tests using various magnetic nanofibrous membranes in accordance with various embodiments of the present disclosure.

After the 5 day culture in the DMEM/F12 and 10% PBS solution, the cells were fixed and fluorescent stained with 4',6-diamidino-2-phenylindole (DAPI) and 488 fluorochrome for cytoplasm. Cells attached to both the pure polycaprolactone nanofibrous membrane and the one with magnetic nanoparticles embedded. FIG. 8 includes images of the mouse cell viability test for 5 days: frame (A) shows cells on polycaprolactone nanofibers (2× magnifications), frame (B) shows cells on magnetic nanoparticle embedded nanofibers (2× magnification), frame (C) shows cells on polycaprolactone nanofibers (40× magnification), and frame (D) shows cells on magnetic nanoparticle embedded nanofibers (40× magnification). The magnetic nanoparticle embedded nanofibers exhibited superior cell viability with respect to the polycaprolactone nanofibers. The magnetic nanofibrous membranes 103 show a much higher cell attachment and cell viability results as shown in FIG. 8.

Figure 9:
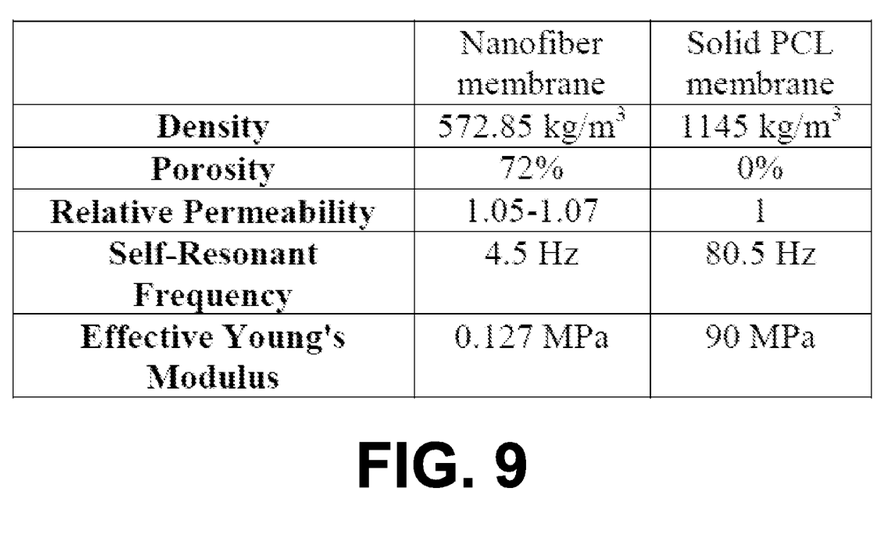
FIG. 9 is a table comparing mechanical characteristics of a magnetic nanofibrous membrane and a solid polycaprolactone (PCL) membrane in accordance with various embodiments of the present disclosure.

The magnetic nanoparticles embedded nanofibrous membrane 103 had a lower density, a lower self-resonant frequency, and a lower effective Young's modulus due to its nanoporous morphology compared with its solid counterpart. The mechanical properties of both nanofibrous and solid membranes are summarized in the table in FIG. 9.

Magnetic nanofibrous membranes were fabricated by electrospinning a solution including iron oxide nanoparticles and polycaprolatone (PCL). The resonant frequency and mechanical properties of nanofibrous membranes were examined compared with those of a solid polycaprolatone membrane. The active scaffold dimension was designed for the effective proliferation of stem cells. Cell culture on the fabricated magnetic nanofibrous scaffold showed increased cell viability compared to a pure polycaprolatone nanofibrous scaffold. Cell culture with active membrane operation is also possible.

It should be emphasized that the described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A nanofibrous membrane, comprising:
   one or more electrospun nanofibers forming a layer of nanofibers affixed to a support structure, the layer of nanofibers extending across an opening of the support structure in a substantially planar orientation and affixed to the support structure along an edge of the opening by a non-toxic glue; and
   a plurality of magnetic nanoparticles embedded in the one or more electrospun nanofibers of the layer of nanofibers,
   where the layer of nanofibers deflects out-of-plane within the opening of the support structure in response to exposure to a magnetic field passing through the opening of the support structure, where the support structure is a machined printed circuit board (PCB) O-ring with the opening.

2. The nanofibrous membrane of claim 1, wherein the magnetic field is time varying.

3. The nanofibrous membrane of claim 1, wherein the deflection of the layer of nanofibers is controlled by the magnetic field.

4. The nanofibrous membrane of claim 1, wherein the layer of nanofibers is a tissue scaffold.

5. The nanofibrous membrane of claim 4, wherein the layer of nanofibers affixed to the support structure has a resonant frequency of deflection in a range of about 4 Hz to about 5 Hz.

6. The nanofibrous membrane of claim 1, wherein the plurality of magnetic nanoparticles comprise iron oxide nanoparticles.

7. The nanofibrous membrane of claim 1, wherein the one or more electrospun nanofibers comprise a biodegradable polymer.

8. The nanofibrous membrane of claim 7, wherein the one or more electrospun nanofibers comprise polycaprolactone.

9. The nanofibrous membrane of claim 1, wherein the support structure is configured to deliver or detect electrical signals to or from cells on the nanofibrous membrane.

10. The nanofibrous membrane of claim 1, wherein the magnetic field is generated by a magnetic field generator positioned below the nanofibrous membrane.

11. The nanofibrous membrane of claim 10, wherein magnetic flux of the magnetic field is maintained less than 10 Gauss.

12. The nanofibrous membrane of claim 1, wherein variation of the magnetic field produces a mechanical oscillation of the layer of nanofibers affixed to the support structure in a range from about 50 nm to about 240 nm.

13. The nanofibrous membrane of claim 1, wherein the plurality of magnetic nanoparticles are about 5% wt of the one or more electrospun nanofibers.

14. The nanofibrous membrane of claim 1, wherein the plurality of magnetic nanoparticles comprise one or more of nickel, cobalt, or neodymium.

15. The nanofibrous membrane of claim 4, wherein variation of the magnetic field produces a mechanical oscillation of the layer of nanofibers affixed to the support structure that is within 1% of a cell volume size of cells when on the tissue scaffold.

16. The nanofibrous membrane of claim 1, wherein the support structure comprises a first portion and a second portion, and the layer of nanofibers is affixed between the first portion and the second portion of the support structure by the non-toxic glue.

* * * * *